United States Patent [19]

Schäpel

[11] Patent Number: 4,466,936

[45] Date of Patent: Aug. 21, 1984

[54] PRODUCTION OF MOLDS USING GEL COMPOSITIONS WITH DEPOT ACTION BASED ON A POLYURETHANE MATRIX AND RELATIVELY HIGH MOLECULAR WEIGHT POLYOLS

[75] Inventor: Dieter Schäpel, Cologne, Fed. Rep. of Germany

[73] Assignee: Bayer Aktiengesellschaft, Leverkusen, Fed. Rep. of Germany

[21] Appl. No.: 502,850

[22] Filed: Jun. 9, 1983

Related U.S. Application Data

[62] Division of Ser. No. 342,035, Jan. 22, 1982, Pat. No. 4,404,296.

[30] Foreign Application Priority Data

Feb. 3, 1981 [DE] Fed. Rep. of Germany ... 3103499
Feb. 3, 1981 [DE] Fed. Rep. of Germany ... 3103500

[51] Int. Cl.$^3$ ............................................. B29C 1/02
[52] U.S. Cl. .................................... 264/225; 264/222; 264/331.19; 264/337
[58] Field of Search ................ 523/105, 109, 122, 123, 523/130; 524/308, 311, 314, 377, 732, 762, 773; 264/222, 225, 331.19, 337

[56] References Cited

U.S. PATENT DOCUMENTS 3,360,495 12/1967 Muller et al. ...................... 260/33.2
3,822,238 7/1974 Blair et al. .
3,975,350 8/1976 Hudgin et al. .
4,131,667 12/1978 Lovell et al. ......................... 264/225
4,341,875 7/1982 Visger et al. ................... 264/331.19

FOREIGN PATENT DOCUMENTS 16652 10/1980 European Pat. Off. .
2347299 4/1975 Fed. Rep. of Germany .
2754249 6/1978 Fed. Rep. of Germany .
289915 7/1953 Switzerland .
1478000 6/1977 United Kingdom .

OTHER PUBLICATIONS

Saunders & Frisch, *Polyurethanes: Chemistry & Technology*, Part I, p. 262.
R. L. Whistler, Industrial Grime, Academic Press, Inc., New York, 1973, pp. 49-114, 473-494, 619-729.

*Primary Examiner*—James B. Lowe
*Attorney, Agent, or Firm*—Gene Harsh; Joseph C. Gil; Lyndanne M. Whalen

[57] ABSTRACT

A polyol gel is made from 15-62 wt. % (based on the sum of polyurethane matrix plus dispersing agent) of a high molecular weight covalently cross-linked polyurethane matrix; 85-38 wt. % (based on the sum of polyurethane matrix plus dispersing agent) of a liquid dispersing agent which is firmly bonded to the matrix; and optionally, active ingredients, fillers, additives, catalysts, and mixtures thereof. The liquid dispersing agent is a polyhydroxyl compound having a molecular weight of between 1,000 and 12,000 and an OH number between 20 and 112. This dispersing agent should have virtually no hydroxyl compounds having a molecular weight below 800 present. These gel compositions may be used to make mold impressions and highly stable active-ingredient releasing compositions.

5 Claims, No Drawings

PRODUCTION OF MOLDS USING GEL COMPOSITIONS WITH DEPOT ACTION BASED ON A POLYURETHANE MATRIX AND RELATIVELY HIGH MOLECULAR WEIGHT POLYOLS

This application is a continuation of application Ser. No. 342,035 filed Jan. 22, 1982 now U.S. Pat. No. 4,404,296 issued Sept. 13, 1983.

BACKGROUND OF THE INVENTION

The present invention relates to a polyurethane matrix-containing gel composition and a process for the production thereof. This gel composition may include active ingredients which ingredients may be released from the matrix to the surrounding environment. This gel composition may be used in making impressions for molding.

Gel compositions are known to those in the art. Such compositions have been used as support media for active ingredients which ingredients are given off to the surrounding environment over a period of weeks or even months. (See e.g. U.S. Pat. Nos. 3,822,238 and 3,975,350). Polyurethane polyurea gels containing water and/or alcohol which perfumed substances have been incorporated have also been prepared. For example, German Offenlegungsschrift No. 2,521,265 describes use of aqueous gels as carriers for a wide variety of materials such a pharmaceuticals, biocidal agents and perfumes. However, the known aqueous gels have the disadvantage that many agents (particularly biocidal agents) are subject to fairly rapid decomposition in the presence of water so that the length of time during which gels containing these agents are active is greatly reduced.

It is also known to incorporate active substances into solid and/or foamed high molecular weight polyurethanes (e.g. Swiss Pat. No. 289,915) but such high molecular weight polyurethanes are disadvantageous in that a high proportion of the liquid agents incorporated therein remain in the polyurethane (due to the molecular structure) and can not therefore be given off to the surrounding environment. Further, solid active ingredients may be used in such foamed polyurethanes only to a very limited extent. Active ingredients which are not volatile do not migrate out of the polyurethane mass whereas those solid agents that are highly volatile may only diffuse out of the foam for a very short period of time and in very small quantities.

Aqueous gels have been used in many other industrial applications (See e.g. R. L. Whistler, Industrial Gums, Academic Press, Inc. NY 1973 and DE-AS (German Published Specification) No. 2,347,299). Because of their capability for a high degree of accuracy in making impressions, these gels have been found to be particularly useful in replicating molded articles. In such replication process, the gel-forming composition is poured over the object of which an impression is to be taken. After formation of the gel, the article is removed from the gel-mold which is a cavity corresponding in volume to that of the original article. Such molds have many applications. In the field of denistry, for example, agar-agar gel is frequently used as a replicating composition. These aqueous compositions are, however, disadvantageous in that: (1) gellation requires a long period of time and must be carried out under specific process conditions; (2) elasticity of the gel is not high enough to permit removal of thin projections and undercuts from the mold; and (3) dimensional stability is poor (as can be seen from the fact that on open storage of the gel mold, a change in the proportions of the mold occurs after a brief period of time) due to water evaporation.

Anhydrous compositions useful in making mold impressions are also known. Such compositions may be based, for example, on silicones. These compositions may be prepared by mixing a pre-polymer with a small amount of a cross-linking agent. This mixture is then poured over the object of which an impression is to be taken. The original object is removed after the mold composition has hardened leaving a mold with a cavity in which casts of the original articles may be produced. These anhydrous compositions are, however, disadvantageous in that: (1) the viscosity of the mold composition is too high to form accurate impressions of objects having fine indentations and undercuts in the surface; and (2) the reaction time is much too long. Attempts to shorten the reaction time by increasing the proportion of cross-linking agent results in a significant degree of mold shrinkage.

SUMMARY OF THE INVENTION

It is an object of the present invention to provide a gel composition and a process for the production thereof.

It is another object of the present invention to provide a gel composition which is storage stable for extended periods of time.

It is also an object of the present invention to provide an anhydrous polyurethane matrix polyol gel composition containing at least one active ingredient and a process for the production thereof.

It is another object of the present invention to provide a gel composition containing at least one active ingredient which composition uniformly releases the active ingredient to the surrounding environment, has a high concentration of active ingredient, and which admits of efficient migration of the active ingredient.

It is a further object of the present invention to provide a molding composition capable of producing a highly accurate mold impression.

It is yet another object of the present invention to provide a gel composition made from a partially cross-linked polyurethane matrix containing a relatively high proportion of a high molecular weight polyol which composition facilitates and controls migration and release of an active ingredient to the surrounding environment.

These and other objects which will be apparent to those skilled in the art are accomplished with a polyol gel comprising: (a) 15-62 weight % (based on (a)+(b)) of a high molecular weight covalently cross-linked polyurethane matrix; (b) 85-38 weight % (based on (a)+(b)) of a liquid dispersing agent which is firmly bonded in the matrix by secondary valence forces; and optionally (c) fibers and/or additives and/or catalysts suitable for an isocyanate polyaddition reaction and/or active ingredients. The liquid dispersing agent is a polyhydroxy compound having a molecular weight of between 1000 and 12,000 and an OH number of between 20 and 112. This dispersing agent should have virtually no hydroxy compounds having a molecular weight below 800 present. Mold impressions of an original article may be made by pouring such a gel-forming composition over the original article, allowing the gel-forming composition to set and subsequently removing the original article.

DETAILED DESCRIPTION OF THE INVENTION

The gels of the present invention are obtained by reacting one or more higher-functional, higher-molecular weight polyol with a quantity of organic diisocyanate and/or polyisocyanate such that a characteristic isocyanate number of about 15-60 results. The term "characteristic isocyanate number" as used herein means the equivalence ratio $(NCO/OH) \times 100$. This gel-forming reaction may be carried out in the presence of appropriate catalysts, active ingredients, fillers and/or additives. These gels, which may be synthesized from a covalently cross-linked polyurethane matrix and one or more polyols which are firmly bonded therein, are formed only when the isocyanate component or polyol component has a certain minimum functionality and when the polyol is essentially free of any polyol having an OH number greater than 112 or a molecular weight below 800 (preferably below 1,000).

More specifically, the gels of the present invention are made up of (a) from 15 to 62 weight %, preferably 20 to 57 weight %, most preferably 25 to 47 weight % (based on the sum of polyurethane matrix+dispersing agent) of a high-molecular weight covalently crossed-linked polyurethane matrix and (b) 85 to 38 weight %, preferably 80 to 43 weight %, most preferably 75 to 53 weight % (based on the sum of polyurethane matrix+dispersing agent) of a liquid dispersing agent which is firmly bonded in the matrix by secondary valence forces. Up to 50 weight % (based on the sum of polyurethane matrix+dispersing agent) active ingredient may be included in the gel-forming composition. From 0 to 100 weight % (based on the sum of polyurethane matrix+dispersing agent) of one or more fillers and/or additives and/or an appropriate catalyst (i.e. one of the catalysts known to be suitable for a polyurethane-forming reaction) may also be used in making these gels.

It is essential to the present invention that the liquid dispersing agent be one or more polyhydroxy compounds having a molecular weight between 1,000 and 12,000 (preferably between 1,700 and 6,000), and an OH number between 20 and 112, preferably between 28 and 84, most preferably between 30 and 56. This dispersing agent should contain virtually no hydroxy compounds having a molecular weight below 800.

The gels of the present invention may be prepared by the direct reaction of polyisocyanate with the high molecular-weight polyhydroxy compound if the isocyanate number is in the range of from approximately 15 to 60, preferably from 20 to 55, most preferably from 25 to 45, and the polyurethane-forming components (isocyanate and hydroxy compounds) are both polyfunctional. If both of these conditions (i.e. isocyanate number and polyfunctionality) are not met, liquid OH-prepolymers of the type known to those skilled in the art of polyurethane chemistry are formed instead of gels.

In general, the lower the characteristic isocyanate number, the higher the functionality of the polyurethane-forming components used in the present invention must be. It should also be noted that the polyol employed may have primary and/or secondary OH groups. If mixtures of polyols with primary and secondary OH groups are used, the primary polyhydroxy compounds react preferentially with the isocyanate component, so that "functionality of the polyol component" is essentially the same as the OH functionality of the primary polyol. However, in the context of the present invention, the total quantity of the polyol component must be included when calculating the characteristic isocyanate number.

In preparing the polyurethane matrix, the reactants should be such that the product of the isocyanate functionality and the polyol functionality is at least 5.2, preferably at least 6.2, preferably at least 8, and most preferably at least 10. The minimum acceptable value of 5.2 may be attained when the characteristic isocyanate number is at the upper end of the acceptable range (i.e. approximately 60), if a mixture of approximately equivalent quantities of primary and secondary hydroxy compounds is employed as the polyol component. In this case, the polyol component with primary OH groups reacts virtually quantitatively with the isocyanate. Specifically, if a diisocyanate is used, a polyol component having a functionality of 2.6 is necessary to achieve the 5.2 minimum.

Where the characteristic isocyanate number is 50 and a single primary or secondary polyol component is used, the product of the functionalities should be at least 6.2, preferably 8. Where the characteristic isocyanate number is 30 and a single primary or secondary polyol component is used, the product of the functionalities should be at least 9, preferably at least 10. More detail in this respect can be ascertained from the Examples which follow.

The present invention also relates to gels containing active ingredients. Such gels are made up of from 15 to 62 weight %, preferably 20-57 weight % and most preferably 25 to 47 weight % (based on the sum of polyurethane matrix+dispersing agent), of a high molecular weight covalently cross-linked polyurethane matrix, 85 to 38 weight %, preferably 80 to 43 weight %, most preferably 75 to 53 weight % (based on the sum of polyurethane matrix+dispersing agent) of a liquid dispersing agent bound to the matrix by subsidiary valency forces, an active ingredient and from 0 to 100 weight % (based on the sum of polyurethane matrix+dispersing agent) of fillers and/or additives and/or appropriate catalysts.

The liquid dispersing agent is one or more polyhydroxy compound having a molecular weight of from 1000 to 12,000 (preferably from 1700 to 6000) and an OH number of from 20 to 112, preferably from 28 to 84, most preferably from 30 to 56. The dispersing agent should be substantially free from any hydroxyl compound having a molecular weight below 800, preferably below 1,000.

The active ingredient should be used in an amount such that from 0.1 to 50 weight %, preferably 0.5 to 35 weight %, most preferably 0.75 to 25 weight % of the gel composition is active ingredient.

These gels may, as already mentioned above, be obtained in a surprisingly simple manner by direct reaction of polyisocyanate with the relatively high molecular weight polyhydroxy compounds in the presence of the active ingredients. The characteristic isocyanate index of the polyurethane thus produced should be in the range of about 15 to 60, preferably 20 to 55, most preferably 25 to 45. The polyurethane-forming components (polyisocyanates and polyhydroxyl compounds) employed must be polyfunctional, i.e. the product of the isocyanate functionality and the polyol functionality must be greater than 4, so that one or more components having a functionality greater than 2 must necessarily be in the polyurethane-forming reaction. If this polyfunctionality requirement is not met, a liquid prepolymer rather than a gel is obtained from the covalently cross-linked polyurethane matrix and unreacted polyol.

The present invention also relates to a process for taking impressions of objects in which a gel-forming composition is poured over the object of which an impression is to be taken (i.e. the original article). After gel formation, the original article is removed. The gel forming composition is made up of one or more diisocyantes and/or polyisocyanates, one or more polyhydroxy compounds having a molecular weight between 1,000 to 12,000 (preferably between 1,700 and 6,000) and an OH number between 20 and 112, preferably between 28 and 84, most preferably between 30 and 56, and if appropriate, catalysts (suitable for the reaction between isocyanate groups and hydroxyl groups) and/or known fillers and additives. This mixture should be essentially free of hydroxyl compounds having a molecular weight below 800. The characteristic isocyanate number of the mixture should be between 15 and 60 and the product of the functionalities of the polyurethane-forming components should be at least 5.2, preferably 6.2, more preferably 8, and most preferably 10. It is preferred that the gel-forming composition be applied in several layers, which layers may have different compositions The consistency of the gels of the present invention may be between a jelly-like or gelatine state and a solid jelly and may be in a more or less highly elastic state. This wide range is possible by varying the characteristic isocyanate numbers and the functionality of the starting components as illustrated by the Examples given below.

It is particularly surprising that the gels of the present invention are exceptionally stable. Even after relatively long periods of storage, no substantial phase separation occurs. The polyol dispersing agent must therefore be very firmly bonded in the gel. In fact, if appropriate reactants are employed, a gel in which the dispersing agent is not given off at temperatures of 50°–100° C. can be obtained. Further, since gels of the present invention are insoluble in dimethylformamide, it can be assumed that at least some of the polymer chains in these gels are covalently cross-linked and that the remaining portion of the polymer chain is bonded by secondary valence forces and mechanical linkages. Even after the polyol reaction with the polyisocyanate, a significant amount of unreacted polyol is still present in the polyurethane matrix.

Besides serving as a synthesizing component for the polyurethane matrix, the above-described polyol or polyols also act as the dispersing agent of the present invention. The higher-molecular weight polyols which may be used in the present invention include polyhydroxy polyesters, polyhydroxy polyethers, polyhydroxy polythioethers, polyhydroxy polyacetals, polyhydroxy polycarbonates or polyhydroxy polyesteramides within the above-mentioned molecular weight and OH number ranges. Suitable polyol compounds are liquid at room temperature or slightly above room temperature and are known to those skilled in the art.

Reaction products of polyhydric (preferably dihydric and, if appropriate, also trihydric) alcohols with polybasic (preferably dibasic) carboxylic acids are examples of suitable polyesters. In addition to free polycarboxylic acids, the corresponding polycarboxylic acid anhydrides or corresponding polycarboxylic acid esters or low alcohols, or mixtures thereof, may also be used for the preparation of the polyesters. The polycarboxylic acids can be of an aliphatic, cycloaliphatic, aromatic and/or heterocyclic nature and, if appropriate, can be substituted (e.g. by halogen atoms) and/or unsaturated.

Examples of carboxylic acids and derivatives thereof suitable for the production of appropriate polyesters include: succinic acid, adipic acid, suberic acid, azelaic acid, sebacic acid, phthalic acid, isophthalic acid, trimellitic acid, phthalic acid anhydride, tetrahydrophthalic acid anhydride, hexahydrophthalic acid anhydride, tetrachlorophthalic acid anhydride, endomethylenetetrahydrophthalic acid anhydride, glutaric acid anhydride, maleic acid, maleic acid anhydride, fumaric acid, dimerized and trimerized unsaturated fatty acids (if appropriate mixed with monomeric unsaturated fatty acids, such as oleic acid) dimethylterephthalate and bis-glycol terephthalate. Ethylene glycol, 1,2-propylene glycol, 1,3-propylene glycol, 1,4-butylene glycol, 2,3-butylene glycol, hexane-1,6-diol, octane-1,8-diol, neopentyl glycol, 1,4-bis-hydroxymethylcyclohexane, 2-methyl-1,3-propanediol, glycerol, trimethylolpropane, hexane-1,2,6-triol, butane-1,2,4-triol, trimethylolethane, pentaerythritol, quinitol, mannitol, sorbitol, formitol and methyl glycoside, diethylene glycol, triethylene glycol, tetraethylene glycol and higher polyethylene glycols, dipropylene glycol and higher polypropylene glycols, and dibutylene glycol and higher polybutylene glycols are examples of suitable polyhydric alcohols. Suitable polyesters may have some terminal carboxyl groups. Polyesters of lactones (for example, ε-caprolactone) or of hydroxy-carboxylic acids (for example ω-hydroxycaproic acid) may also be employed.

Polyethers which are suitable to the present invention have at least two, generally two to eight, and preferably two to three, hydroxyl groups. Appropriate polyethers are known to those in the art. Such polyethers may be prepared, for example, by polymerization of epoxides, such as ethylene oxide, propylene oxide, butylene oxide, tetrahydrofuran, styrene oxide or epichlorohydrin, alone or in the presence of a Lewis catalyst, such as BF$_3$. Such polyethers may also be produced by the addition of epoxides (preferably ethylene oxide and propylene oxide), either in a mixture or successively onto starting components with reactive hydrogen atoms. Suitable starting components having reactive hydrogen atoms include water, alcohols, ammonia and amines, such as ethylene glycol, 1,3- propylene glycol, 1,2-propylene glycol, trimethylolpropane, glycerol, sorbitol, 4,4'-dihydroxydiphenylpropane, aniline, ethanolamine and ethylenedimine. Sucrose polyethers, such as those described, for example, in German Auslegeschriften Nos. 1,176,358 and 1,064,938, and polyethers started from formitol or formost described, for example in German Offenlegungsschrift Nos. 2,639,083 and 2,737,951 are also suitable to the present invention. Those polyethers which have predominantly (up to 90 weight % relative to all OH groups present in the polyether) primary OH groups are usually preferred. Polybutadienes which have OH groups are also suitable to the present invention.

Among the polythioethers which may be used in the practice of the present invention, the condensation products of thiodiglycol with itself and/or with other glycols, dicarboxylic acids, formaldehyde, aminocarboxylic acids or aminoalcohols are particularly advantageous. Accordingly, the products of such condensation reactions may include mixed polythioethers, polythioether esters or polythioether ester-amides.

Compounds which can be prepared from glycols, such as diethylene glycol and triethylene glycol, 4,4'- dihydroxy-ethoxydiphenyldimethylmethane, hexanediol and formaldehyde are examples of suitable polyacetals. Appropriate polyacetals may also be prepared by the polymerization of cyclic acetals, such as, trioxane (German Offenlegungsschrift 1,694,128).

Suitable polycarbonates having hydroxyl groups are known to those in the art. Such polycarbonates can be prepred, for example, by the reaction of diols (such as propane-1,2-diol, butane-1,4-diol and/or hexane-1,6-diol, diethylene glycol, triethylene glycol, tetraethylene glycol or thiodiglycol) with diaryl carbonates (for example, diphenyl carbonate) or phosgene (German Auslegeschriften Nos. 1,694,080; 1,915,908 and 2,221,751; German Offenlegungsschrift No. 2,605,024).

The polyester amides and polyamides which may be used as the polyol of the present invention include, for example, the predominantly linear condensates obtained from polybasic saturated or unsaturated carboxylic acids, and/or anhydrides thereof, and polyhydric saturated and unsaturated aminoalcohols, diamines, polyamines and mixtures thereof. Polyhydroxy compounds which already contain urethane groups or urea groups, as well as optionally modified natural polyols may also be used.

Polyhydroxy compounds in which high-molecular polyadducts or polycondensates or polymers are contained in finely dispersed or dissolved form can also be employed according to the invention, if appropriate. Polyhydroxy compounds of this type may be obtained by means of polyaddition reactions (for example reactions between polyisocyanates and amino-functional compounds) or polycondensation reactions (for example between formaldehyde and phenols and/or amines) which are allowed to take place in situ in the above-mentioned compounds having hydroxyl groups. Processes of this type are described, for example, in German Auslegeschriften Nos. 1,168,075 and 1,260,142, and in German Offenlegungsschriften Nos. 2,324,134; 2,423,984; 2,512,385; 2,513,815; 2,550,796; 2,550,797; 2,550,833; 2,550,862; 2,633,293 and 2,639,254. However, it is also possible (see, e.g., U.S. Pat. No. 3,869,413 or German Offenlegungsschrift No. 2,550,860) to mix a prepared aqueous polymer dispersion with a polyhodroxy compound and then to remove the water from the mixture.

Polyhydroxy compounds modified by vinyl polymers may be obtained by the polymerization of styrene and acrylonitrile in the presence of polyethers (U.S. Pat. Nos. 3,383,351; 3,304,273; 3,523,093 and 3,110,695; German Auslegeschrift No. 1,152,536) or polycarbonate polyols (German Pat. No. 1,769,795; U.S. Pat. No. 3,637,909). These modified polyhydroxy compounds are also suitable for use in the present invention. When polyether polyols which have been modified in the manner disclosed in German Offenlegungsschriften No. 2,442,101; 2,644,922 and 2,646,141, by grafting with vinyl phosphonic acid esters and, if appropriate, (meth)acrylonitrile, (meth)acrylamide or OH-functional (meth)acrylic acid esters are used in the present invention, gels which have very good flame repellancy are obtained. Further examples of hydroxy compounds which may be used in practicing the present invention are described, for example, in High Polymers, Volume XVI, "Polyurethanes, Chemistry and Technology", edited by Saunders-Frisch, Interscience Publishers, New York, London, Volume I, 1962, pages 32–42 and pages 44–54, and Volume II, 1964, pages 5–6 and 198–199; and in Kunststoff-Handbuch (Plastics Handbook), Volume VII, Vieweg-Hochtlen, Carl-Hanser-Verlag, Munich, 1966, for example on pages 45–71. It is, of course, possible to employ mixtures of the above-mentioned compounds, for example a mixture of polyethers and polyesters.

The polyhydroxyl polyethers of the type described above which are known to those in the art and which have 2–6 (preferably 2–3) hydorxyl groups per molecule, are preferred as the higher-molecular weight polyol for the present invention. Polyhydroxy polyethers which have terminal ethylene oxide units (and therefore primary hydroxyl groups) are preferred components either alone or in a mixture with other polyethers. In the polyhydroxy polyether compounds, the proportion of ethylene oxide sequences in the polyether should preferably be at least 10 weight %, preferably 15 weight %, most preferably at least 20 weight %. Polypropylene ether polyols containing at least 20 weight % ethylene oxide and in which at least 15 weight % of the hydroxyl end groups are primary hydroxyl groups are particularly preferred polyols.

The higher-molecular weight polyols should be chosen or mixed together so that the dispersing agent contained in the gels of the present invention is liquid at room temperature. These polyols are used in amounts such that the polyol content in the gel-forming mixture is about 80–99 weight % (preferably 85–98 weight %) of the gel-forming polyurethane starting components.

On the preparation of the gels of the present invention, aliphatic, cycloaliphatic, araliphatic, aromatic and heterocyclic polyisocyanates (such as those described by W. Siefken in Justus Liebigs Annalen der Chemie, 562, pages 75 to 136) may be employed. Such polyisocyanates generally correspond to the formula

$$Q(NCO)_n$$

in which
n=2–4, preferably 2, and Q denotes an aliphatic hydrocarbon radical having 2–18 (preferably 6–10) carbon atoms, a cycloaliphatic hydrocarbon radical having 4–15 (preferably 5–10) carbon atoms; an aromatic hydrocarbon radical having 6–15 (preferably 6–13) carbon atoms or an araliphatic hydrocarbon radical having 8–15 (preferably 8–13) carbon atoms.

Specific examples of such isocyanates are ethylene diisocyanate, tetramethylene-1,4-diisocyanate, hexamethylene-1,6-diisocyanate, dodecane-1,12-diisocyanate, cyclobutane-1,3-diisocyanate, cyclohexane-1,3-diisocyanate, cyclohexane-1,4-diisocyanate and mixtures of these isomers; 1-isocyanato-3,3,5-trimethyl-5-isocyanato-methylcyclohexane (German Auslegeschrift 1,202,785 and U.S. Pat. No. 3,401,190), hexahydrotoluylene-2,4-diisocyanate and hexahydrotoluylene-2,6-diisocyanate, and mixtures of these isomers; hexahydrophenylene-1,3-diisocyanate and/or hexahydrophenylene-1,4-diisocyanate, perhydro-diphenylmethane-2,4'-diisocyanate and/or perhydro-diphenylmethane-4,4'-diisocyanate, phenylene-1,3-diisocyanate, phenylene-1,4-diisocyanate, toluylene-2,4-diisocyanate and toluylene-2,6-diisocyanate, and mixtures of these isomers; diphenylmethane-2,4'-diisocyanate and/or diphenylmethane-4,4'-diisocyanate and naphthylene-1,5-diisocyanate.

The following are also examples of compounds which are suitable to the practice of the present invention: triphenyl-methane-4,4',4''-triisocyanate; polyphenyl-polymethylene polyisocyanates (obtained by aniline/formaldehyde condensation and subsequent phosgenation as described in British Pat. Nos. 874,430 and 848,671); m-isocyanatophenylsulfonyl isocyanates and p-isocyanatophenylsulfonyl isocyanates (according to U.S. Pat. No. 3,454,606); perchlorinated aryl polyisocyanates (German Auslegeschrift No. 1,157,601 (U.S. Pat. No. 3,277,138)); polyisocyanates having carbdodiimide groups (as described in German Patent Specification No. 1,092,007 (U.S. Pat. No. 3,152,162) and in German Offenlegugnsschriften Nos. 2,504,400; 2,537,685 and 2,552,250); norbornane diisocyanates (according to U.S. Pat. No. 3,492,330); polyisocyanates having allophanate groups (as described in British Pat. No. 994,890, Belgian Pat. No. 761,626 and Dutch Patent Application No. 7,102,524); polyisocyanates having isocyanurate groups (as described in U.S. Pat. No. 3,001,973, in German Patent Specifications Nos. 1,002,789, 1,222,067 and 1,027,394 and in German Offenlegungsschriften Nos. 1,929,034 and 2,004,048); polyisocyanates having urethane groups (as described in Belgian Pat. No. 752,261 or in U.S. Pat. Nos. 3,394,164 and 3,644,457); polyisocyanates which have acylated urea groups (prepared according to German Pat. No. 1,230,778); polyisocyanates having biuret groups (as described in U.S. Pat. Nos. 3,124,605, 3,201,372 and in British Pat. No. 889,050); polyisocyanates prepared by telomerization reacitons, (as described in U.S. Pat. No. 3,654,106); polyisocyanates having ester groups, (as mentioned in British Pat. Nos. 965,474 and 1,072,956, in U.S. Pat. No. 3,567,763 and in German Pat. No. 1,231,688); reaction products of the above-mentioned isocyanates with acetals according to German Patent Specification No. 1,072,385; and polyisocyanates which contain polymeric fatty acid esters (according to U.S. Pat. No. 3,455, 883).

It is also possible to employ the distillation residues which have isocyanate groups and which are produced in industrial isocyanate processes, particularly if the residues are dissolved in one or more of the previously mentioned polyisocyanates.

All of the above-mentioned diisocyanates and polyisocyanates may, of course, also be employed as mixtures.

Toluylene diisocyanates and diphenylmethane diisocyanates are examples of preferred diisocyanates. Biuretized and trimerized hexamethylene-1,6-diisocyanate and crude diphenylmethane diisocyanates are also examples of preferred polyisocyanates.

The diisocyanate and/or polyisocyanate content in the gel-forming mixture should be approximately 1–20 weight %, preferably 2–15 weight % (based on the total weight of the mixture).

The catalysts which may be used in producing the gels of the present invention are those known to catalyze the reaction between hydroxyl groups and isocyanate groups. Specific examples of suitable catalysts are tertiary amines, such as triethylamine, tributylamine, N-methylmorpholine, N-ethylmorpholine, N-(coconut alkyl)-morpholine, N,N,N',N'-tetramethyl-ethylenediamine, 1,4-diazabicyclo-(2,2,2)octane, N-methyl-N'-dimethylaminoethylpiperazine, N,N-dimethyl-benzylamine, bis-(N,N-diethylaminoethyl)adipate, N,N-dimethylcyclohexylamine, N,N,N',N'-tetramethyl-1,3-butanediamine, N,N-dimethyl-β-phenyl-ethylamine, pentamethyldiethylenetriamine, 1,2-dimethylimidazole and 2-methylimidazole. Mannich bases which are in themselves known and are derived from secondary amines (such as dimethylamine) and aldehydes (preferably formaldehyde) or ketones (such as acetone, methyl ethyl ketone or cyclohexanone) and phenols (such as phenol, nonylphenol or bisphenol) are also suitable catalysts.

Sila-amines containing carbon-silicon bonds, as described in German Pat. No. 1,229,290 (corresponding to U.S. Pat. No. 3,620,984) are also suitable catalysts. 2,2,4-trimethyl-2-silamorpholine and 1,3-diethylamino-methyl-tetramethyl-disiloxane are specific examples of such catalysts.

Organic metal compounds, particularly organic tin compounds, can also be used according to the invention as catalysts. Tin (II) salts of carboxylic acids (such as tin (II) acetate, tin (II) octoate, tin (II) ethyl-hexoate and tin (II) laurate) and the tin (IV) compounds (for example, dibutyl-tin oxide, dibutyl-tin dichloride, dibutyl-tin diacetate, dibutyl-tin dilaurate, dibutyl-tin maleate and dioctyl-tin acetate) are preferred organic tin compounds.

All of the above-mentioned catalysts can, of course, be used as mixtures. Further representatives of catalysts which may be used in the present invention and details on the mode of action of these catalysts are described in Kunststoff-Handbuch (Plastics Handbook), Volume VII, edited by Vieweg and Hochtlen, Carl-Hanser-Verlag, Munich, 1966 on pages 96 to 102.

The catalysts should preferably be used in a quantity of between 0.05 and 10 weight % of the total weight of the gel.

Substances and groups of substances which serve as active ingredients in making the active ingredient containing gels of the present invention include biocides, pharmaceuticals, perfumes, inks, cleaning agents, age resistors, plant nutrients, antifouling agents and preservatives, detergents and detergent auxiliaries.

Examples of suitable biocides are bactericides, fungicides, algicides, herbicides, viruscides, larvacides, nematicides, ectoparasiticides such as tickicides or insecticides. Appropriate pharmaceuticals and/or substances for the care and protection of the skin include antimycotics, anti-allergic agents, antirheumatics, antiseptics, local anaesthetics, substances to increase the local blood supply, venous agents, wound balms, and substances to cure itching and dermatitis, agents containing moisture, substances absorbing UV radiation, bacteriostatics, cosmetics and deodorants (such as halogen phenols or salicylic acid derivatives) and disinfectants. Naturally occurring active ingredients such as ethereal oils (e.g. eucalyptus oil), menthol oils, pheromones, vitamins and enzymes may also be used.

Natural and synthetic perfume substances including ethereal oils, perfumes and odoriferous substances made of known individual odoriferous components or compositions such as anisole, oil of bergamot, oil of camphor, clove oil, lemon grass oil, lavender oil, peppermint oil, rose oil and cinnamon oil are also appropriate active ingredients. Other suitable components are described in German Offenlegungsschrift No. 2,521,265.

Stamping and staining inks and substances for deleting ink and crayon marks may also be used in the gel of the present invention.

Cleaning and dressing agents for leather and plastics, e.g. colorless or colored waxes and stain removers may also be used.

Age resistors, e.g. antioxidants such as dodecyl gallate or tert.-butyl-substituted phenols, UV absorbents; light protective agents; antistatics such as ethoxylated alkyl phenols and preservatives are also appropriate active ingredients.

Plant nutrients such as inorganic salt mixtures, substances for keeping cut flowers fresh and growth regulators may also be active ingredients present in the gels of the present invention.

Antifouling agents and wood preservatives, e.g. copper, mercury or tin compounds in powder form, pentachlorophenols and dinitrophenols; detergents and detergent auxiliaries, such as alkylaryl-sulfonates, fatty alcohol sulfonates, fatty alcohol-ethylene oxide adducts, fabric softeners, fabric conditioners, antifoaming agents, brightening agents and photohardenable mixtures may also be used in the gels of the present invention.

The quantity of active substance in the gel compositions of the present invention is generally between 0.1 and 50 weight %, preferably 0.5 to 35 weight % and most preferably 0.75 to 25 weight % (based on the total weight of the gel composition). This quantity may, however, be lower (e.g. less than 0.01 weight %) when highly active additives such as pheromones are used.

The choice of appropriate active substances may be limited in cases where some active substances contain groups which are so highly reactive that the active substances will become more or less completley fixed under the conditions of the gel forming polyurethane reaction and will therefore remain fixed so that they are no longer capable of being released.

the fillers and additives which may optionally be included in the gels of the present invention are materials which are known to those skilled in the art of polyurethane chemistry. Examples of appropriate materials are fillers and short fibers with an inorganic or organic basis, metal powders, coloring agents, such as dyestuffs and colored pigments, water-binding agents, surface-active substances, flame-proofing agents and liquid extenders (e.g. substances with a boiling point of above 150° C.). Barite, chalk, gypsum, kieserite, sodium carbonate, zeolite, titanium dioxide, cerium oxide, quartz sand, kaolin, carbon black and micro glass beads are examples of appropriate inorganic fillers. Powders based on polystyrene, polyvinyl chloride, urea/formaldehyde and polyhydrazodicarboxamide (e.g. from hydrazine and toluylene diisocyanate) can be used as organic fillers. Glass fibers of 0.1-1 mm length or fibers of organic origin, such as polyester fibers, polyamide fibers, aramide and carbon fibers are examples of suitable short fibers. Metal powders, for example, iron powder or copper powder may also be used concomitantly in gel formation. The dyestuffs or colored pigments which are known to be useful in coloration of polyurethanes (for example, iron oxide pigments, chromium oxide pigments pigments which have a phthalocyanine basis or monoazo basis) can be used to impart the desired coloration to the gels of the present invention. Zeolites are preferred water-binding agents. Cellulose powder, activated charcoal, silicic acid preparations and chrysotileasbestos are examples of appropriate surface-active substances.

Sodium polymetaphosphates may be added to the gel-forming composition as flame-proofing agents. Alkyl-substituted, alkoxy-substituted or halogen-substituted aromatic compounds (such as dodecylbenzene, m-dipropoxybenzene or o-dichlorobenzene), halogenated aliphatic compounds (such as chlorinated paraffins), organic carbonates (such as propylene carbonate), carboxylic acid esters (such as dioctyl phthalate), dodecylsulfonic acid esters and organic phosphorus compounds (such as tricresyl phosphate) may be used as liquid extenders. Higher-molecular weight polyols, the hydroxyl groups of which are etherified, esterified or urethanized can also be employed as liquid extenders.

The content of fillers and extenders in the gels according to the invention can be up to 50 weight % of the total weight of the gel. It is preferred, however, that they be used in quantities less than 25 wt. % of the gel.

A wide variety of auxiliary agents may also be used to adapt the formulations of the gel compositions according to the invention to their particular purpose. Thus, for example, if pharmaceuticals are to be incorporated in the gels according to the invention, resorption auxiliaries such as phospholipides, solubilizing agents such as polyethylene glycols or polypropylene glycols, emulsifiers such as glycero-fatty acid esters, spreading agents such as silicone oils, fatty acid esters or triglycerides, and skin care substances such as 2-octyl-dodecanol may be added at the stage of gel formation.

If biocidal formulations are to contain solid active substances, it may be advantageous to add spreading agents and in particular plasticizers such as dibutylphthalate at the stage of gel formation. The following substances may be used as spreading agents: silicone oils of various viscosities; fatty acid esters such as lauric acid hexyl ester, dipropylene glycol pelargonate; esters of medium length branch chained fatty acids with saturated $C_{16}$-$C_{18}$ fatty alcohols, such as isopropylmyristate, isopropylpalmitate; caprylic/caproic acid esters of saturated fatty alcohols of chain length $C_{12}$-$C_{18}$; isopropylstearate; oleic acid decyl ester; waxy fatty acid esters such as adipic acid diisopropyl ester, triglycerides such as caprylic/caproic acid triglyceride, triglyceride mixtures of $C_8$-$C_{12}$ vegetabl fatty acids or other specially selected natural fatty acids; and partial glyceride mixtures or monoglycerides; also fatty alcohols such as isotridecylalcohol, 2-octyl-dodecanol or oleyl alcohol; or fatty acids such as oleic or stearic acid. Particularly suitable spreading oils are isopropylmyristate, iospropylstearate, isopropylpalmitate, lauric acid hexyl ester, oleic acid decyl ester, dibutylstearate, dibutyl sebacate, paraffin oil, ethyl hexyl palmitate/stearate and isotridecylstearate.

Production of the gel compositions containing active ingredients according to the invention may be carried out continuously or batchwise. The method chosen depends inter alia on the particular form to be given to the gels according to the invention to suit the purpose for which they are to be employed.

The preparation of the gels of the present invention may be accomplished in a variety of ways. Specifically, these gels may be produced by a one-shot process or a prepolymer process. In the one-shot process, all the components (i.e., polyols, diisocyanates and/or polyisocyanates, catalysts and, if appropriate, fillers and extenders) are simultaneously added together and mixed intensively with one another. It is preferred that any active ingredient employed be dissolved or dispersed in the polyol component before the other reactants are combined with the polyol.

There are two prepolymer processes which may be used to produce the gels of the present invention. In one such process, an isocyanate prepolymer is first prepared by reacting a portion of the polyol with the total quantity of isocyanate used in the gel formation. The remaining portion of polyol and, if appropriate, fillers and additives are then added to the prepolymer, and the resultant mixture intensively mixed. In another prepolymer process, the total quantity of polyol used in the gel formation is first reacted with a portion of the total amount of isocyanate to give a hydroxy prepolymer. The remaining portion of isocyanate is then mixed into the prepolymer mixture. Where an active ingredient is to be present in the polyurethane product, it is desirable that the active ingredient be present in the polyol before the prepolymer is formed.

A procedure which is particularly advantageous according to the invention is a variation of both the one-shot and the hydroxy prepolymer processes. In this preferred process, the polyol or polyol mixture, any fillers and additives, the catalyst and two different diisocyanates or polyisocyanates are added together in one charge and are intensively mixed. One of the isocyanates is aromatic and the other isocyanate is aliphatic. It is believed that, due to the greatly differing reactivities of the two isocyanates, a hydroxy prepolymer is first formed, which prepolymer then reacts, within minutes, with the other isocyanate to form a gel. Gels with a particularly high viscosity are obtained by this process.

In the above-described procedures, the conveying, metering and mixing of the individual components or component mixtures may be carried out using devices which are known to those skilled in the art.

It is particularly surprising that even when polyurethanes having relatively low characteristic isocyanate numbers (for example 30) and a polyol component with uniformly reactive OH groups (so that a selective reaction of a part of the polyol component with the polyisocyanate is not to be expected), gels with a high-molecular weight, cross-linked matrix that are insoluble in dimethylformamide are obtained. One skilled in the art would expect these materials to form polyols modified by urethane groups (OH-prepolymers).

To obtain a good matrix structure, the reaction between polyol and polyisocyanate should be carried out at a relatively low temperature, e.g. below 50° C, preferably at room temperature.

If molded articles are to be produced, it is advisable to employ a batchwise process. If, however, the polyurethane gel according to the invention is to be produced in separate pieces of suitable dimensions, a continuous method may be preferable. In the latter case, an endless foil or plate is first produced, and may subsequently be subdivided into individual pieces.

In a continuous method, the mixture which is capable of gelling may also be sprayed, case or applied by a knife coating process before it solidifies by gel formation. Such a mixture particularly one containing an active ingredient may be applied to various materials based on natural or synthetic raw materials, e.g. to mats, fleeces, woven and knitted fabrics, foam foils or plastics foils or panels, or it may be cast into suitable molds.

The conditions during gel formation may be varied to produce either cellular or non-cellular gels. If, for example, air is churned into the gel forming mixture, foam gels are obtained.

The gels of the present invention may be used to make molds in accordance with techniques known to those skilled in impression technology or replication technology. In such processes, the mixture which is capable of forming a gel may be poured or sprayed before it solidifies. The gel can be reinforced by a variety of materials based on natural or crude synthetic substances, such as fleece, knitted fabric, mesh fabric, woven fabric, foam films, plates or mats. Such reinforcing materials may be incorporated in the interior of the gel or applied as an external layer on the gel. The gel composition may also be applied to the model from which an impression is to be taken in successive layers. In this latter process, a compact gel layer is first applied to the model for an accurate impression. A composition capable of forming a gel which is greatly enriched with air, for example, may then be applied as the second layer. Such an air-enriched composition forms a foam gel which gel reduces the weight of the gel mold. A filler-containing gel for reinforcing the gel mold may also be applied as the second layer in such a process.

The gels of the present invention are suitable for taking accurate impressions of models made of a wide variety of materials such as gypsum, wood, concrete, steel, plastics, epoxides, polyurethanes, stone , ceramic and metals (such as copper and iron).

A major advantage of the polyol gels of the present invention over known anhydrous impression compositions (such as compositions based on silicones) is the lower viscosity of the gel-forming mixture. Because of this low viscosity, impressions may be obtained of very fine indentations in the model surface. A further advantage of the new gels is that they have shorter reaction times and thus make it possible to remove the model of which an impression is to be taken from the mold more rapidly than was previously possible. The preparation of a mold containing a cavity from the gels of the present invention thus requires a smaller expenditure of time.

The polyol gels of the present invention are an improvement over aqueous gels (such as agar-agar gel) because of their higher elasticity. This high elasticity makes it possible to obtain impressions of thin projections and undercuts in a trouble free manner because the gel mold does not tear when the model from which an impression was taken is removed. A further advantage of the gels of the present invention over gels with an aqueous basis is their dimensional stability on open storage.

The polyol gels of the present invention may also be used as injection-molding compositions for medical and biological preparations (e.g. beetles, butterflies, internal organs and tissue samples). Some of the synthetic resins which have been employed for this purpose are based on epoxide resins. These epoxide resins are, however, disadvantageous in that the heat which evolves during curing is undesirably high and they are susceptible to a high degree of shrinkage. Gels made from natural materials, such as gelatines, exhibit inadequate long-term consistency (i.e. a disintegration of such gels can occur after only a few months).

The gels of the present invention are particularly useful for making molds because they are transparent, do not turn yellow and they retain their consistency over periods of months or even years.

Due to their high elasticity the gels of the present invention can be used as shock-absorbing elements, such as safety shock-absorbers in lift installations or for car bumper systems; as pressure-distributing elements, such as for example for padding between prostheses and parts of the body; or for printing rollers; as water-soakable elements, such as for example for the sealing of shaft walls in underground construction; or for piping to prevent penetration of water; for switching systems for automatically operated water-spraying installations; as a filling substance for breast prostheses; as an embedding or coating substance for light transmitting fibers for the optical transmission of messages as well as for liquid crystals, for display surfaces; as insulating material for impact noise, for example in the automobile sector or machine construction; and as a filler material for hot compresses or cold compresses for medical applications.

The gel compositions of the present invention which contain active ingredients may be used in a wide variety of forms, e.g. as granulates, foils, panels, blocks, rods or molded articles. The choice depends upon the particular purpose the compositions are to serve and upon the concentration at which the active ingredients are required to be released. These active ingredients may diffuse from the gels over a period of weeks or months and, depending upon their volatility, they may be released into a gaseous phase and/or they may be brought into contact with solid or liquid materials (e.g. the skin of animals or water) to be released to the surrounding environment.

These active ingredient-containing gels are suitable for a wide variety of purposes such as plasters containing dermatological substances to be attached to the skin, as insecticide containing bands or plates to destroy flies and vermin, to remove ticks and fleas from animals, as plates and shaped articles containing perfume for scenting rooms, as deodorizing compositions for transmission to the skin, as printing or stamping plates which have a low tendency to dry out, as shoe cleaning materials for the application of dyes and waxes, as insecticide-containing tree rings to protect against insects, as lubricants with an antistatic effect, etc..

One important advantage of the gels containing active ingredients of the present invention over aqueous gels containing active ingredients is the greater stability of active reagents which are liable to be hydrolyzed (such as insecticides, plant protective agents, perfumes or pharmaceuticals) during storage and during the active period of the gels.

Another important advantage of the new gel compositions is that even solid or difficultly volatile active ingredients incorporated in them will migrate. Therefore, if they have a certain solubility in the polyols used as dispersing agents, such active ingredient containing gels will remain active for a long period of time. In this respect, the gels of the present invention provide a valuable improvement compared with known solid and foamed polyurethanes (which are prepared by addition of the reactive components in quantities corresponding to an isocyanate index of 70 to 200 and in which there are no significant quantities of free polyol) in that the high density of cross-linking in the known polyurethanes prevents the outward migration of solid active ingredients.

Having thus described our invention, the following Examples are given by way of illustration. The quantities given in these examples are weight percentages or parts by weight unless otherwise indicated.

EXAMPLES

The polyisocyanates employed in the Examples were:

Polyisocyanate 1

Hexamethylene 1,6-diisocyanate

Polyisocyanate 2

Commercial biuretized hexamethylene 1,6-diisocyanate having an average NCO functionality of 3.6, an NCO content of 21% and an average molecular weight (number average) of approximately 700 ("Desmodur" (Trade Mark of Bayer AG)).

Polyisocyante 3

Isomer mixture composed of 80% of toluylene 2,4-diisocyanate and 20% of toluylene 2,6-diisocyanate.

Polyisocyanate 4

4,4'-Diisocyanatodiphenylmethane liquefied by pre-polymerization with tripropylene glycol, average NCO functionality: 2.50; NCO content: 23%.

Polyisocyanate 5

Prepolymer composed of 159 parts of polyisocyanate 3 and 2,000 parts of polyether 9 (see the table below). NCO content: 3.9%.

Polyisocyanate 6

Prepolymer of 159 parts of polyisocyante 3 and 1200 parts of a polyether with OH number 28 prepared by the chemical addition of 60 parts of ethylene oxide and 40 parts of propylene oxide to glycerol.

The polyether polyols used in the Examples and referred to by number are summarized in the Table which follows. In the Table, TMP represents trimethylolpropane; PG represents propylene 1,2-glycol; Gly represents glycerol and PE represents pntaerythritol.

| Polyol No. | Propylene oxide % | Ethylene oxide % | Starter molecule | OH number | OH functionality |
|---|---|---|---|---|---|
| 1 | 80 | 20 | TMP | 36 | 3 |
| 2 | 100 | — | PG | 56 | 2 |
| 3 | 45 | 55 | TMP | 56 | 3 |
| 4 | 100 | — | TMP | 56 | 3 |
| 5 | 90 | 10 | TMP | 56 | 3 |
| 6 | 85 | 15 | TMP | 56 | 3 |
| 7 | 83 | 17 | TMP | 34 | 3 |
| 8 | 100 | — | Sorbitol | 46 | 6 |
| 9 | 40 | 60 | Gly | 28 | 3 |
| 10 | 100 | — | TMP/PG (84:16) | 46 | 2.75 |
| 11 | 100 | — | PE | 45 | 4 |
| 12 | 50 | 50 | PG | 56 | 2 |
| 13 | 80 | 20 | PG | 28 | 2 |
| 14 | 82 | 18 | TMP | 35 | 3 |
| 15 | 73 | 27 | Sorbitol | 30 | 6 |
| 16 | 63 | 37 | Sorbitol | 30 | 6 |

Polyol 17 is a partly branched polyester of adipic acid, diethylene glycol and TMP. Average molecular weight: approximately 2,000; average OH functionality: 2.3.

EXAMPLE 1

(a) Preparation of the gel 100 parts of polyether 1, 5 parts of polyisocyanate 2, and 1.5 parts of dibutyl-tin dilaurate, were intensively mixed for 1 minute. After 10 minutes, a cloudy, elastic gel, which was free of tackiness on its surface, was obtained.

(b) Preparation of a mold from the gel

The mixture thus-produced could be poured for a period of 1 to 5 minutes (counted from the beginning of mixing). This mixture was poured over an article composed of gypsum. After 15 minutes (counted from the beginning of mixing) the gypsum model could be removed. A gel mold, the volume and contours of which corresponded to those of the gypsum model which had been removed, was obtained.

EXAMPLE 2

(a) Preparation of the gel 10 parts of polyether 1, 40 parts of polyether 2, 50 parts of polyether 3, 1.5 parts of dibutyl-tin dilaurate and 6 parts of polyisocyanate 2 were intensively mixed for 1 minute. After 15 minutes, a clear, elastic gel, the surface of which was free from tackiness formed.

(b) Preparation of a mold from the gel

The mixture prepared in (2a) was used to take an impression of a molding composed of epoxide. After approximately 20 minutes, the epoxide model which had been encased in the gel could be removed from the gel mold. The gel mold had a cavity which was identical in contour with the epoxide model.

EXAMPLE 3

In accordance with the procedure of Example 2, a gel and a mold were prepared from 10 parts of polyether 4, 50 parts of polyether 5, 40 parts of polyether 6 and 1.5 parts of dibutyl-tin dilaurate and 6 parts of polyisocyanate 2.

EXAMPLE 4

3,500 parts of polyether 3, 700 parts of polyether 7 and 2,800 parts of polyether 2 were stirred at a temperature of 22° C. by means of a laboratory mixer with a disc stirrer to give a clear solution. 301 parts of polyisocyanate 2 were added to the solution, while stirring to assure that the polyisocyanate was well distributed. 105 parts of dibutyl-tin dilaurate were added to the thus-produced cloudy solution and the mixture was mixed intensively for 3 minutes.

The whitish cloudy solution was poured into a prepared, square casing of polyurethane film of film thichness 0.2 mm, with an edge length of 45 cm, and the film casing was welded to make it airtight. The gel pad thus prefabricated was laid on an even base and left alone to undergo a gel reaction. When gelation was complete the gel pad reached its full mechanical strength and could be fully loaded. It was a soft body which retained its shape and could be deformed under pressure. If the deforming force was removed, the gel pad returned to its initial shape.

EXAMPLE 5

3,500 parts of polyether 3, 700 parts of polyether 7, 2,800 parts of polyether 2 and 35 parts of dibutyl-tin dilaurate were mixed in a vessel at 22° C., until the mixture was homogeneous. The mixture was fed to a static mixer by means of a gear pump. 273 parts of polyisocyanate 2 were simultaneously fed to this mixture from a separate storage container (by means of another gear pump) in a manner such that at any time the mixing ratio of the two components was identical and corresponded to the proportions of the total quantities.

The whitish cloudy solution flowing from the static mixer was poured into a square casing, and a gel pad in the form of a cushion was prepared therefrom, by the procedure described in Example 4.

EXAMPLE 6

1,000 parts of polyether 1, 50 parts of polyisocyanate 2 and 15 parts of dibutyl-tin dilaurate were intensively mixed at room temperature for 1 minute, with the aid of a laboratory stirrer (a disc stirrer). After 10 minutes, a cloudly, elastic, shape-retaining gel was formed. This gel could be slightly deformed when subjected to a force and resumed its initial state after removal of the deforming force.

EXAMPLE 7

1,000 parts of polyether 8, 25 parts of polyisocyanate 3 and 30 parts of dibutyl-tin dilaurate were intensively mixed at room temperature for 1 minute, with a laboratory stirrer (a disc stirrer). A soft, elastic, shape-retaining gel was obtained. This gel could be deformed slightly by a force acting upon it but it resumed its initial shape upon removal of the deforming force.

EXAMPLE 8

1,000 parts of polyether 8, 45 parts of polyisocyanate 4 and 30 parts of dibutyl-tin dilaurate were reacted in accordance with the procedure described in Example 7. A soft, elastic, shape-retaining gel which could be sightly deformed by a force acting upon it but resumed its initial shape after removal of the deforming force was obtained.

EXAMPLE 9

1,000 parts of polyether 9 were reacted with 50 parts of polyisocyanate 4 and 30 parts of dibutyl-tin dilaurate in accordance with the procedure described in Example 7. A soft, elastic, shape-retaining gel, which could be slightly deformed by a force acting upon it and resumed its initial state upon removal of the deforming force was obtained.

EXAMPLE 10

This Example illustrates use of softening agents in making a gel according to the present invention. 490 parts of polyether 3, 480 parts of dibutyl adipate, 30 parts of polyisocyanate 2 and 15 parts of dibutyl-tin dilaurate were reacted in accordance with the procedure described in Example 7. A soft, elastic, shape-retaining gel, which could be slightly deformed by a force acting upon it and which resumed its initial state upon removal of the deforming force was obtained.

EXAMPLE 11

This Example also illustrates use of softening agents. 508 parts of polyether 3, 450 parts of an alkylsulfonic acid ester of phenol, 27 parts of polyisocyanate 2 and 15 parts of dibutyl-tin dilaurate were reacted in accordance with the procedure of Example 7 to give a soft, elastic, shape-retaining gel, which could be slightly deformed by the effect of a force acting upon it but resumed its starting state after removal of the deforming force.

EXAMPLE 12

484 parts of polyether 3, 450 parts of an alkylsulfonic acid ester of phenol, 51 parts of polyisocyanate 4 and 15 parts of dibutyl-tin dilaurate were reacted in accordance with the procedure described in Example 7 to give a soft, elastic, shape-retaining gel, which could be slightly deformed by the effect of a force acting upon it and which resumed its starting state after removal of the deforming force.

EXAMPLE 13

Gels were prepared in accordance with the procedure described in Example 1 from materials of varying OH or NCO functionality. The characteristic isocyanate number was 50 in each case.

The properties of the gels thus obtained are summarized in the table which follows: "Liquid" denotes that no gel structure was formed due to the fact that the functionality was too low.

Polyisocyanate 1, polyisocyanate 2 or mixtures thereof having the given average NCO functionality were used as the isocyanate component; the polyol component was polyol 2, 10 or 11, or 1:1 mixtures of 2 and 10 or 10 and 11.

| NCO | Functionality OH | | | | |
|---|---|---|---|---|---|
| | 2 | 2.3 | 2.75 | 3.25 | 4 |
| 2 | | | | liquid | very soft |
| 2.1 | | | | very soft | soft |
| 2.2 | | | liquid | soft | hard |
| 2.3 | | | very soft | soft | |
| 2.4 | | | very soft | | |
| 2.6 | | liquid | soft | | |
| 2.8 | | very soft | | | |
| 3.1 | | soft | | | |
| 3.6 | liquid | hard | | | |

EXAMPLE 14

The dependence of the gel consistency upon the OH and NCO functionality was studied for the characteristic isocyanate number 30 in the manner described in Example 13. The polyols 10, 11, 8, or a 1:1 mixture of 11 and 8, were used as the hydroxyl component. The results were as follows:

| NCO | Functionality OH | | | |
|---|---|---|---|---|
| | 2.75 | 4 | 4.8 | 6 |
| 2 | | | | liquid |
| 2.1 | | | liquid | very soft |
| 2.15 | | | liquid | soft |
| 2.2 | | | very soft | soft–hard |
| 2.3 | | | very soft | hard |
| 2.4 | | liquid | soft | hard |
| 2.8 | | very soft | soft | hard |
| 3.6 | very soft | soft | | |

EXAMPLE 15

The dependence of the gel consistency upon the characteristic isocyanate number and the NCO functionality was investigated in the manner described in Example 13. A 1:1 mixture of polyols 2 and 12 was employed as the polyol component, and mixtures of the polyisocyanates 1 and 2 having the indicated average NCO functionality were employed as the isocyanate component. The results were as follows:

| Characteristic Number | Functionality NCO | | | |
|---|---|---|---|---|
| | 2.6 | 2.8 | 3.0 | 3.2 |
| 55 | very soft | | | |
| 52.5 | liquid | | | |
| 50 | liquid | soft | | |
| 47.5 | liquid | very soft | soft | hard |

EXAMPLE 16

Dependence of the gel consistency on the NCO functionality at constant characteristic isocyanate number (50) and OH functionality (3) was studied.

| Experiment A: | polyol component: | polyol 6 |
| | isocyanate component: | mixtures of polyisocyanates 1 and 2 |
| Experiment B: | polyol component: | polyol 4/polyol 6 (1:1) |
| | isocyanate component: | same as in Experiment A. |

| NCO Functionality | Experiment A | Experiment B |
|---|---|---|
| 2 | liquid | liquid |
| 2.1 | liquid | very soft–soft |
| 2.2 | very soft | soft |
| 2.3 | soft | soft–hard |
| 2.4 | soft–hard | hard |
| 2.6 | hard | hard |
| 2.8 | hard | very hard |

EXAMPLE 17

Dependence of the gel consistency upon the mixing ratio of polyether with primary hydroxyl groups/polyether with secondary hydroxyl groups was studied. The characteristic isocyanate number was 35. The isocyanate component was polyisocyanate 2. The gels were prepared in the manner described in Example 1. The results were as follows:

| Experiment | Polyol 6 (%) | Polyol 4 (%) | Gel consistency |
|---|---|---|---|
| A | 0 | 100 | very soft |
| B | 5 | 95 | soft |
| C | 15 | 85 | soft–hard |
| D | 25 | 75 | hard |
| E | 35 | 65 | very hard |
| F | 45 | 55 | hard |
| G | 75 | 25 | hard |
| H | 100 | 0 | soft–hard |

EXAMPLE 18

The quantity of polyol 4 (which does not react to any significant extent with the other components) which could be added (for an otherwise identical recipe of the reaction mixture) and still obtain a gel was investigated. As the following table shows, the limit of gel formation for the selected starting components was approximately that at which the composition corresponded (theoretically calculated) to 28% of polyurethane matrix and 72% of free polyol.

| Recipe (parts) | A | B | C | D | E |
|---|---|---|---|---|---|
| Polyol 6 | 35 | 35 | 35 | 35 | 35 |
| Polyol 4 | 65 | 100 | 105 | 120 | 150 |
| Polyisocyanate 2 | 7 | 7 | 7 | 7 | 7 |
| Dibutyl-tin dilaurate | 3 | 3 | 3 | 4 | 5 |
| % polyurethane matrix | 38 | 29 | 28 | 25 | 21 |
| Consistency | very hard gel | very soft gel | very soft gel | gel particles in liquid | liquid |

EXAMPLE 19

Example 18 was repeated using the composition prepared in Example 17G. The limit of gel formation in this case was approximately 27% of polyurethane matrix. The results were as follows:

| Recipe (parts) | A | B | C | D | E |
|---|---|---|---|---|---|
| Polyol 6 | 75 | 75 | 75 | 75 | 75 |
| Polyol 4 | 25 | 65 | 75 | 90 | 100 |
| Polyisocyanate 2 | 7 | 7 | 7 | 7 | 7 |
| Dibutyl-tin dilaurate | 3 | 4.5 | 4.5 | 5 | 5 |
| % polyurethane matrix | 38 | 28 | 26 | 24 | 22 |
| Consistency | hard gel | very soft gel | very soft gel, partially liquid | gel particles in liquid | liquid |

EXAMPLE 20

The minimum characteristic isocyanate number which must be maintained in order to obtain a gel in the reaction with various polyols according to the procedure of Example 1 was investigated for the polyisocyanates 2, 3 and 4. The limiting values of the characteristic isocyanate number which were found are summarized in the table which follows.

| Polyol No. | Polyisocyanate No. 2 | Polyisocyanate No. 4 | Polyisocyanate No. 3 |
|---|---|---|---|
| 8 | 20 | 30 | 32 |
| 15 | 18 | 35 | 37 |
| 11 | 30 | 45 | 47 |
| 3 | 25 | 55 | 60 |
| 9 | 25 | 55 | 65 |
| 10 | 32 | 65 | 70 |
| 12 | 40 | — | — |
| 13 | 50 | — | — |
| 17 | 20 | 50 | 52 |

EXAMPLE 21

Gels and impression compositions were prepared in the manner described in Examples 1 and 2, using formulations given in the table below. The softener used was dibutyl adipate; the catalyst was dibutyl-tin dilaurate.

| Component (parts) | A | B | C | D | E | F | G | H |
|---|---|---|---|---|---|---|---|---|
| Polyol 14 | 100 | 10 | 80 | | | | | |
| Polyol 3 | | | | 50 | 100 | 100 | 50.5 | 100 | 50.5 |
| Polyol 2 | 40 | | | | | | | |
| Polyol 17 | | 20 | | | | | | |
| Softener | | | | | 45 | | | |
| Kaolin | | | | | | | 107.5 | |
| o-Dichlorobenzene | | | | | | | | 45 |
| Catalyst | 1.5 | 1.5 | 1.5 | 1.5 | 1.5 | 1.5 | 1.5 | 1.5 |
| Polyisocyanate 2 | 5 | 5.5 | 7.3 | 2 | | 3 | 6 | 3 |
| Polyisocyanate 5 | | | | | 50 | | | |
| Polyisocyanate 4 | | | 6 | | | | | |

EXAMPLE 22

80 parts of polyether 1, 15 parts of methyl butyrate as perfume substance, 1.2 parts of dibutyl tin dilaurate and 4 parts of polyisocyanate 2 were vigorously mixed for one minute. An elastic gel formed after 15 minutes. This gel, when made into a shape such as a cone, cake or imitation rose, may be used for the long term scenting of cupboards, rooms, motor cars or dustbins.

EXAMPLE 23

10 parts of polyether 1, 40 parts of polyether 2 and 8 parts of a perfume oil (from 60% by weight of isobornyl acetate and 40 parts by weight of the addition product of 10 mol of ethylene oxide with 1 mol of nonyl phenol), 50 parts of polyether 3 and 0.15 parts of K-sorbinate, 1.5 parts of dibutyl-tin dilaurate and 6 parts of polyisocyanate 2 were vigorously mixed for one minute. A clear, elastic gel with a non-stick surface formed after 15 minutes. This gel may be used as air freshener for scenting rooms. The perfume gel retained its structure and activity for months.

EXAMPLE 24

A gel was prepared in a manner described in Example 23 from 10 parts of polyether 4, 50 parts of polyether 5 containing 4 parts of the perfume oil from Example 23, 40 parts of polyether 6 containing 0.18 parts of sodium benzoate as bactericide, 1.5 parts of dibutyl-tin dilaurate and 6 parts of polyisocyanate 2.

EXAMPLE 25

100 parts of polyether 3, 5 parts of triethylene glycol dimethyl ether, 8 parts of perfume oil 83/117 (lemon-like scent; product of Colgate Palmolive Peet Inc., USA), 2.5 parts of dibutyl-tin dilaurate and 8 parts of polyisocyanate 2 were vigorously mixed and poured into an open mold to a height of 3 mm. A foil of gel which was 3 mm in thickness was obtained. This foil was cut up into strips measuring 1.5×10 cm. Such a strip may be attached to the inside of the lid of a package containing 4 to 5 kg of detergent powder. The detergent would thereby be perfumed without risk of destruction of the perfume by constituents of the detergent (oxidizing agents).

EXAMPLE 26

3500 parts of polyether 3 containing 350 parts of pentachlorophenol, 700 parts of polyether 7 containing 14 parts of K-sorbinate, 2800 parts of polyether 2 mixed with 50 parts of a high molecular weight polyethylene oxide, and 35 parts of dibutyl tin dilaurate were homogeneously mixed in a stirrer vessel at 22° C.

The mixture was delivered to a static mixer by a gear wheel pump. At the same time, 473 parts of polyisocyanate 2 were delivered to this mixer from a separate container by means of another gear wheel pump at such a rate that the proportions of components in the mixture remain constant and equal to the proportions of the total quantities. The cloudy milky solution leaving the static mixer was poured into a square package. A soft, dimensionally stable gel which could be deformed under pressure was obtained on completion of the gel forming reaction. This gel may be used as deodorant stick to prevent the odor of perspiration caused by bacterial decomposition.

EXAMPLE 27

75 parts of polyether 1, 20 parts of o,o-dimethyl-o-(2,2-dichlorovinyl)-phosphoric acid ester (DDVP, insecticide), 1.2 parts of dibutyl-tin dilaurate and 3.8 parts of polyisocyanate 2 were vigorously mixed for one minute. An elastic gel formed after about 10 minutes. Used in the form of a strip inserted in a perforated plastic container, this gel may serve as insecticidal gel for the long term gassing of the atmosphere, e.g. to destroy insects or cockroaches in kitchens.

EXAMPLE 28

1000 parts of polyether 8 containing 100 parts of the insecticide DDVP (described in Example 27), 45 parts of polyisocyanate 3 and 30 parts of dibutyl tin dilaurate were vigorously mixed for one minute at room temperature, using a laboratory stirrer (stirrer disc). A soft, elastic, dimensionally stable gel was obtained, which gel could easily be deformed by pressure.

EXAMPLE 29

100 parts of polyether 9 containing 4.0 parts of hexachlorophene and 0.48 parts of p-hydroxybenzoic acid ethyl ester were reacted with 5.0 parts of polyisocyanate 4 and 2.8 parts of dibutyl tin dilaurate to produce a soft, elastic, dimensionally stable gel. The gel may be painted on skin to prevent bacterial decomposition of perspiration.

EXAMPLE 30

100 parts of polyether 1 at a temperature of 70° C., 30 parts of 2-isopropoxyphenyl-N-methyl carbamate (an insecticide), 60 parts of isopropylmyristate, 5 parts of permethric acid pentafluorobenzyl ester (an insecticide), 2 parts of dibutyl tin dilaurate, 0.3 parts of iron oxide pigment and 5.5 parts of polyisocyanate 2 were vigorously mixed. The reaction mixture was poured into an open mold lined with synthetic leather until it formed a layer 5 mm thick. When the gel had hardened, it was cut up into strips (15 mm in width) consisting of a decorative leather layer and a gel layer containing the active ingredients. These strips fitted with a buckle may be used as neckbands against fleas and ticks in domestic animals such as cats and dogs.

EXAMPLE 31

Gels were prepared in the manner of Example 22, varying the OH functionality and isocyanate functionality of the starting components but the isocyanate index was 50 in each case. The properties of the resulting gels are summarized in the following Table. The isocyanate components used were polyisocyanate 1, polyisocyanate 2 and mixtures thereof with the given average isocyanate functionality. The polyol components were polyols 10 or 11 or 1:1 mixtures of 2 and 10 or 2 and 11. 5 wt. % lavender oil was used as aroma in the polyol in each case. Gels acting as aroma carrier with long term release were obtained.

| NCO/OH → | NCO/OH Functionality: | | | | |
|---|---|---|---|---|---|
| | 2 | 2.3 | 2.75 | 3.75 | 4 |
| ↓ | | | | | |
| 2 | ↑ | ↑ | ↑ | liquid | very soft* |
| 2.1 | ↑ | ↑ | ↑ | very soft* | soft** |
| 2.2 | ↑ | ↑ | liquid | soft** | hard** |
| 2.3 | ↑ | ↑ | very soft* | soft** | |
| 2.4 | ↑ | ↑ | very soft* | | |
| 2.6 | ↑ | liquid | soft** | | |
| 2.8 | ↑ | very soft* | | | |
| 3.1 | ↑ | soft** | | | |
| 3.6 | liquid | hard** | | | |

*according to the invention
**preferred according to the invention

EXAMPLE 32

The dependence of the gel consistency upon the functionality was investigated for an isocyanate index of 30 in the manner described in Example 31. The hydroxyl components used were polyols 10, 11 and 8 and a 1:1 mixture of 11 and 8, and the polyols contained 4 wt. % lavender oil in each case.

| NCO/OH → | Functionality: | | | |
|---|---|---|---|---|
| | 2.75 | 4 | 4.8 | 6 |
| ↓ | | | | |
| 2 | ↑ | ↑ | ↑ | liquid |
| 2.1 | ↑ | ↑ | ↑ | very soft* |
| 2.15 | ↑ | ↑ | liquid | soft** |
| 2.2 | ↑ | ↑ | very soft* | soft-hard |
| 2.3 | ↑ | ↑ | very soft* | hard** |
| 2.4 | ↑ | liquid | soft** | hard** |
| 2.8 | liquid | very soft* | soft** | hard* |
| 3.6 | very soft* | soft** | | |

*according to the invention
**preferred according to the invention

EXAMPLE 33

The dependency of the gel consistency upon the isocyanate index and isocyanate functionality was investigated as in Example 31. The polyol component used was a 1:1 mixture of polyols 2 and 12 containing 10 wt. % lavender oil as aroma. The isocyanate components used were mixtures of polyisocyanates 1 and 2 having the given average isocyanate functionality.

| Functionality: NCO/ Index → | 2.8 | 3.0 | 3.2 |
|---|---|---|---|
| ↓ | | | |
| 55 ⎫ comparison | very soft | | |
| 52.5 ⎭ | liquid | | |
| 50 ⎫ according to the invention | soft** | | |
| 47.5 ⎭ | very soft* | soft** | hard** |

*according to the invention
**preferred according to the invention

EXAMPLE 34

Dependence of the gel consistency upon the isocyanate functionality was studied when the isocyanate index was 50 and OH functionality was 3.

| Experiment A: | Polyol component: | Polyol 6 |
| --- | --- | --- |
| | Isocyanate component: | Various mixtures of polyisocyanates 1 and 2. |
| Experiment B: | Polyol component: | Polyol 4/polyol 6 (1:1) |
| | | (containing 8 wt. % methyl butyrate as aroma); |
| | Isocyanate component: | as in Experiment A. |

| Isocyanate Functionality | Experiment A | Experiment B |
| --- | --- | --- |
| 2 | liquid | liquid |
| 2.1 | liquid | very soft to soft |
| 2.2 | very soft* | soft** |
| 2.3 | soft** | soft–hard** |
| 2.4 | soft–hard | hard |
| 2.6 | hard** | hard* |
| 2.8 | hard** | very hard* |

* and ** are as defined for Example 33.

EXAMPLE 35

Dependence of the gel consistency upon the proportion of the mixture of polyethers having primary hydroxyl groups to polyethers having secondary hydroxyl groups were studied. The polyols contained 10 wt. % methyl butyrate. Isocyanate index: 35 Isocyanate component: Polyisocyanate 2 The gels were prepared in the manner described in Example 22.

| Experiment | Polyol 6(%) | Polyol 4(%) | Gel consistency |
| --- | --- | --- | --- |
| A | 0 | 100 | very soft |
| B | 5 | 95 | soft |
| C | 15 | 85 | soft to hard |
| D | 25 | 75 | hard |
| E | 35 | 65 | very hard |
| F | 45 | 55 | hard |
| G | 75 | 25 | hard |
| H | 100 | 0 | soft to hard |

EXAMPLE 36

How much polyol 4 (which takes virtually no part in the reaction) may be added to the reaction mixture in the experiment of Example 35 and still obtain a gel was studied. Aside from variation in the polyol component with respect to polyol 4, the formulation was the same as that used in Example 35 (10 wt. % methyl butyrate in the polyol mixture). As shown in the following Table, the limit of gel formation for the selected starting components is a composition which (calculated theoretically) corresponds to 28 wt. % polyurethane matrix and 72 wt. % free polyol. Attempts to extract the polyol gave virtually the same results as the theoretical calculations.

| Formulation (parts) | | | | | |
| --- | --- | --- | --- | --- | --- |
| Polyol 6 | 35 | 35 | 35 | 35 | 35 |
| Polyol 4 | 65 | 100 | 105 | 120 | 150 |
| Polyisocyanate 2 | 7 | 7 | 7 | 7 | 7 |
| Dibutyl tin dilaurate | 3 | 3 | 3 | 4 | 5 |
| % Polyurethane matrix | 38 | 29 | 28 | 25 | 21 |
| Consistency | very hard* gel | very soft* gel | very soft** gel | gel particles in liquid | liquid |

* and ** have the same meaning as in Example 33.

EXAMPLE 37

Example 14 was repeated using formulation G of Example 35. The limit of gel formation in this case was approximately 27% polyurethane matrix.

| Formulation (parts) | | | | | |
| --- | --- | --- | --- | --- | --- |
| Polyol 6 | 75 | 75 | 75 | 75 | 75 |
| Polyol 4 | 25 | 65 | 75 | 90 | 100 |
| Polyisocyanate 2 | 7 | 7 | 7 | 7 | 7 |
| Dibutyl tin dilaurate | 3 | 4.5 | 4.5 | 5 | 5 |
| % Polyurethane matrix | 38 | 28 | 26 | 24 | 22 |
| Consistency | hard* gel | very soft* gel | very soft gel, partly liquid | gel particles in liquid | liquid |

*according to the invention

EXAMPLE 38

Using polyisocyanates 2, 3 and 4, the minimum isocyanate index which must be observed in order that a gel may be obtained in the reaction with various polyols (with the addition of 3 wt. % methyl butyrate as aroma substance) was investigated by the method of Example 22. The limiting values of isocyanate index found are summarized in the Table below.

| Polyisocyanate No./ → Polyol No. ↓ | 2 | 4 | 3 |
| --- | --- | --- | --- |
| 8 | 20 | 30 | 32 |
| 16 | 18 | 35 | 37 |
| 11 | 30 | 45 | 47 |
| 3 | 25 | 55 | 60 |
| 9 | 25 | 55 | 65 |
| 10 | 32 | 65 | 70 |
| 12 | 40 | — | — |
| 13 | 50 | 50 | 52 |
| 17 | 20 | 50 | 52 |

EXAMPLE 39

100 parts of polyether 1 at a temperature of 70° C., 25 parts of 2-isopropoxyphenyl-N-methylcarbamate (insecticide), 10 parts of 3-phenoxy-4-α-fluoro-cyanobenzyl-2,2-dimethyl-3-[2-(4-chlorophenyl)-2-chlorovinyl]-cyclopropane carboxylate (insecticide), 2.5 parts of dibutyl tin dilaurate and 5.5 parts of polyisocyanate 2 were vigorously mixed. The gel obtained, made up into plates, strips or solid shapes, may be attached in some suitable manner to farm animals such as cattle (for example to the tail, neck, horns orears (earmarks)). This will protect the animals for many weeks against numerous harmful animal parasites (ectoparasites).

EXAMPLE 40

100 parts of polyether 1, 15 parts of diphenyl-acetylenyl-imidazolyl-methane (algicide), 2 parts of dibutyl tin dilaurate and 5 parts of polyisocyanate 2 were vigorously mixed. An elastic gel was obtined after 15 minutes. such a gel may be used to coat, for example, ships, buoys or quay walls in the regions under water to prevent the growth of algae, barnacles, mussels and other forms of marine life.

EXAMPLE 41

100 parts of polyether 3, 5 parts of menthol, 2.5 parts of dibutyl tin dilaurate and 8 parts of polyisocyanate 2 were vigorously mixed. the resulting reaction mixture was poured onto a close meshed, rigid plastic grid of polyethylene where it solidified to form an elastic gel mass within 30 minutes. A menthol-containing strip obtained in this manner may be used for medicinal purposes (e.g., inhalation of menthol).

EXAMPLE 42

100 parts of polyether 1, 5 parts of nonyphenol, 5 parts of dodecylbenzyl dimethylammonium chloride, 1.5 parts of dibutyl tin dilaurate and 5 parts of polyisocyanate 2 were vigorously mixed. The mixture was poured into an open mold measuring $1 \times 2 \times 10$ cm. The rod of gel obtained was placed in a dish measuring $2 \times 2 \times 10$ cm which dish was attached to a toilet bowl in a suitable manner so that a large quantity of water would be poured over the gel each time the bowl is flushed. Long term disinfection of the bowl may thereby be achieved.

EXAMPLE 43

100 parts of polyether 3, 30 parts of potassium dichromate/pentachlorophenol (1:1), 3 parts of dibutyl tin dilaurate and 8 parts of polyisocyanate 2 were vigorously mixed. The reaction mixture obtained was applied as a 5 mm thick layer to a polyester fabric on which it hardened to form a gel. Such coated polyester fabrics may be used as bandages to cover wooden masts at the transition from earth to air to protect the wood against rot.

EXAMPLE 44

100 parts of polyether 3, 15 parts of sodium dodecyl benzene sulfonate, 2.5 parts of dibutyl tin dilaurate and 8 parts of polyisocyanate 2 were vigorously mixed and sprayed onto an open celled foil of polyurethane foam (polyester based) 10 mm in thickness. Such an impregnated foil bonded to a sponge of flexible polyether foam may be used for cleaning purposes.

EXAMPLE 45

100 parts of polyether 3 at a temperature of 40° C., 15 parts of 1-methyl-1-alkylaminoethyl-2-alkyl-imidazolinium-methosulfate (cationic quaternary imidazoline compound of Ashland Chemical Co., U.S.A.; fabric softener), 0.2 parts of Heliofast Yellow C.I. No. 11680, 2 parts of dibutyl tin dilaurate and 8 parts of polyisocyanate 2 were vigorously mixed. The resulting reaction mixture was poured on a polypropylene fleece to form a layer 3 mm in thickness. An elastic gel layer was obtained after about 10 minutes. The fleece coated with gel is suitable for softening fabric in tumbler driers.

What is claimed is:

1. A process for taking an impression of an object in which a gel-forming composition is first poured over the object, the gel-forming composition is permitted to gel, and the object is subsequently removed in which the gel-forming composition comprises:
   (a) a polyisocyanate; and
   (b) a polyhydroxyl compound having a molecular weight between 1,000 and 12,000 and an OH number between 20 and 112 said composition being essentially free of hydroxyl compounds having a moleular weight less than 800, having an isocyanate index between 15 and 60 with the product of the isocyanate and hydroxyl functionalities being at least 5.2

2. The process of claim 1 wherein the gel-forming composition further comprises a catalyst suitable for an isocyanate polyaddition reaction.
3. The process of claim 1 wherein the gel-forming composition further comprises fillers and/or additives.
4. The process of claim 1 wherein the gel-forming composition is applied to the object in several layers.
5. The process of claim 4 wherein each of the several layers is of a different composition.

* * * * *